United States Patent

Horiuchi

[11] 3,931,291
[45] Jan. 6, 1976

[54] PREPARATION OF OPTICALLY ACTIVE ALLETHRORONE VIA ALLETHRONYL ACID PHTHALATE

[75] Inventor: Fukashi Horiuchi, Kawani, Japan

[73] Assignee: Sumitomo Chemical Company, Limited, Osaka, Japan

[22] Filed: Mar. 22, 1974

[21] Appl. No.: 453,997

[30] Foreign Application Priority Data
Mar. 28, 1973 Japan............................ 48-36005
Apr. 18, 1973 Japan............................ 48-44411
June 11, 1973 Japan............................ 48-66039
June 11, 1973 Japan............................ 48-66040

[52] U.S. Cl....... 260/475 N; 260/468 H; 260/586 R
[51] Int. Cl.²........................................ C07C 69/80
[58] Field of Search................... 260/475 R, 475 N

[56] References Cited
UNITED STATES PATENTS
3,201,455   8/1965   Russell et al.................... 260/475 R
3,484,489  12/1969   Kierstead et al................ 260/475 N FOREIGN PATENTS OR APPLICATIONS
2,263,880   7/1973   Germany........................ 260/475 N OTHER PUBLICATIONS
Eliel, *Stereochemistry of Carbon Compounds*, pp. 49–56 (1962).
Fukumaru et al., as cited in Chem. Abstracts, 74, 42127e (1971).
Muller et al., as cited in Chem. Abstracts 69, 2698g (1968).
Bucourt et al., as cited in Chem. Abstracts 72, 31304t (1970).

*Primary Examiner*—Lorraine A. Weinberger
*Assistant Examiner*—Jane S. Myers
*Attorney, Agent, or Firm*—Wenderoth, Lind & Ponack

[57] ABSTRACT

Optically active allethronyl acid phthalate is prepared by reacting (±)-allethronyl acid phthalate of the formula

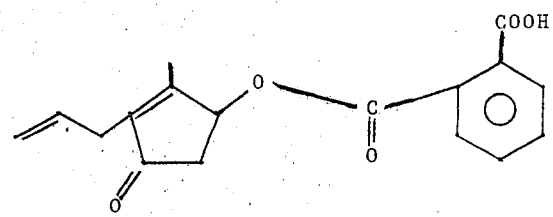

with an optically active amine from the group of α-phenylethylamine of the formula,

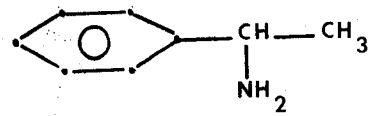

α-phenyl-β-p-tolylethylamine of the formula

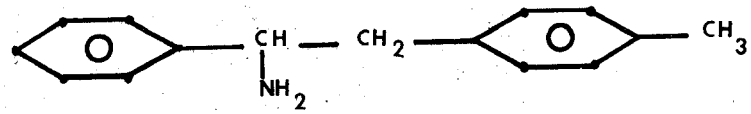

threo-2-dimethylamino-1-(p-nitrophenyl)-1,3-propanediol of the formula

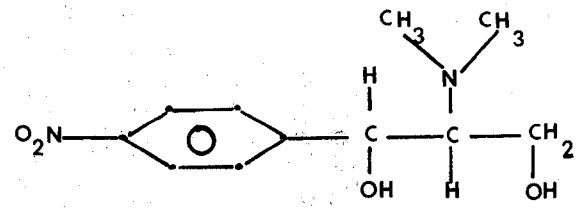

and naphthylethylamine of the formula

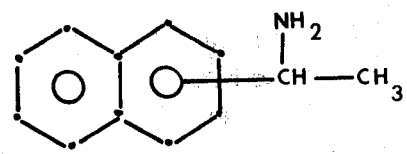

to form diastereomeric salts thereof, and decomposing the resolved salt to obtain the optically active allethronyl acid phthalate.

2 Claims, No Drawings

PREPARATION OF OPTICALLY ACTIVE ALLETHRORONE VIA ALLETHRONYL ACID PHTHALATE

The present invention relates to a method for preparing optically active allethronyl acid phthalate (2-allyl-4-hydroxy-3-methyl-2-cyclopentenone acid phthalate).

More particularly, the present invention relates to a method for preparing optically active allethronyl acid phthalate by reacting (±)-allethronyl acid phthalate represented by the formula,

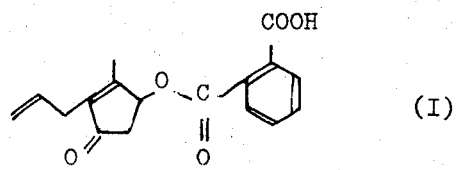

with optically active α-phenylethylamine represented by the formula,

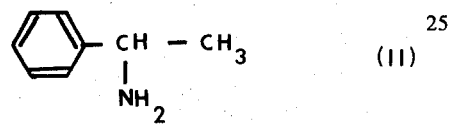

or optically active α-phenyl-β-p-tolylethylamine represented by the formula,

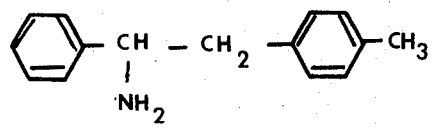

or optically active threo-2-dimethylamino-1-(p-nitrophenyl)-1,3-propanediol represented by the formula,

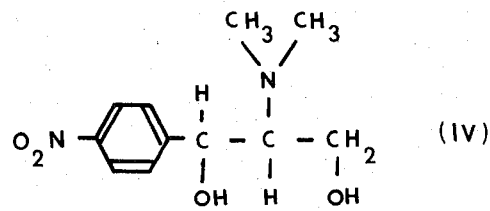

or optically active naphthylethylamine represented by the formula,

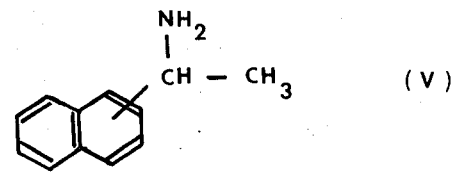

to form diastereoisomeric salts thereof, and then by resolving the salts into optically active allethronyl acid phthalate components by means of fractional crystallization.

Hydrolysis of the optically active allethronyl acid phthalate obtained according to the present method affords optically active allethrolone, and hydrolysis of a racemic allethronyl acid phthalate affords a racemic allethrolone.

The above-mentioned raction processes can be represented by the following schema:

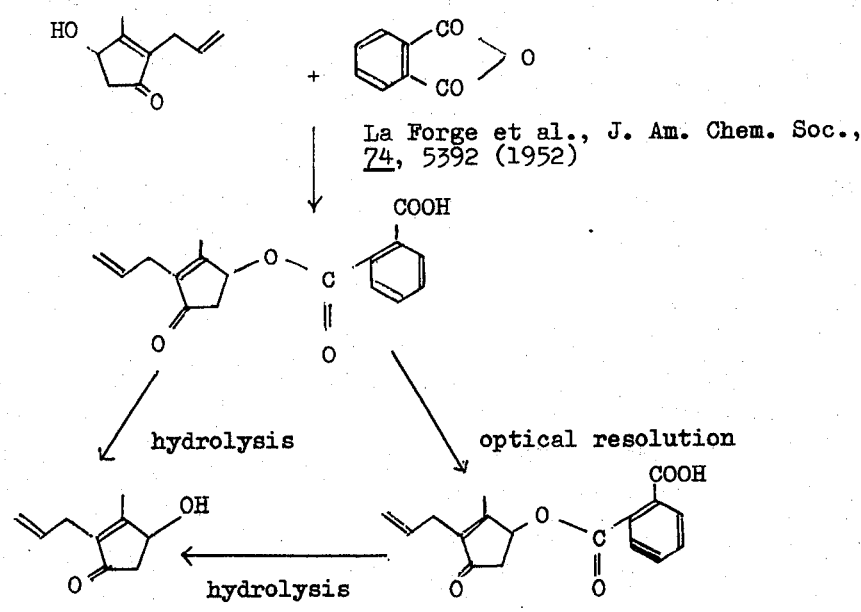

Allethrin (allethronyl chrysanthemate) has widely been used as a low toxic (to mammal) and rapidly effective insecticidal ester which has a similar chemical structure and insecticidal activity to natural pyrethrins. As allethrolone, an alcohol moiety of the allethrin, has an asymmetric carbon atom at the 4-position it is present in two optical isomeric forms. Of the chrysanthemic acid esters of allethrolone, (+)-allethrolone ester is known to have several times greater insecticidal activity than (−)-allethrolone ester. It is, therefore, very important to develop a method for preparing optically active allethrolone industrially advantageously.

The only known method to prepare optically active allethrolone was based on optical resolution of the semicarbazones of diastereoisometic (±)-allethrolonyl (+)-transchrysanthemates by means of fractional crystallization, and cleavage of the separated semicarbazone into the optically active allethrolone (F. B. La Forge et al., J. Org. Chem., 19, 457, 1954). This method, however, can not be applied industrially because it has such a number of difficulties as many reaction steps, complicated operation and low over-all yield.

On the other hand, for optical resolution of a racemic alcohol, a method can most generally be carried out, which consists of resolution of the diastereoisomeric acid phthalates of the alcohol using an optically active amine, and hydrolysis of the resolved half ester into the optically active alcohol.

La Forge et al., in their attempts to apply this method to the optical resolution of allethrolone, studied in details the hydrolysis of allethronyl acid phthalate which is an intermediate in the optically active allethrolone synthesis (F. B. La Forge et al., J. Am. Chem. Soc., 74, 5392, 1952).

They showed that even at the room temperature the said phthalates could be hydrolysed with an excess of caustic soda, i.e. 2.2 equivalents, to afford, no allethrolone at all, but only a dimeric product resulting from the condensation of two allethrolone molecules was obtained. From this fact, the optical resolution of allethrolone via its acid phthalate has been regarded as impossible. Furthermore, they described at the beginning of the report that allethrolone can not generally be regenerated on the hydrolysis of allethrolone carboxylic acid ester. The above-mentioned difficulty of recovery can also be understood sufficiently by the fact that pyrethrolone [2-(2'-4'-pentadienyl)-4-hydroxy-3-methyl-2-cyclopentenone] can not be obtained by the hydrolysis of the pyrethrin [(+)-pyrethronyl (+)-trans chrysanthemate] which has a very similar chemical structure to that of allethrin. So, to obtain pyrethrolone, Standinger and Ruzicka, who could not obtain pyrethrolone by the direct hydrolysis of pyrethrin used a very troublesome process which consisted of the preparation of pyrethrin-semicarbazone, cleavage of the ester linkage by a base-catalyzed ester exchange reaction and decomposition of pyrethrolone-semicarbazone to pyrethrolone with aqueous sodium bisulfate. (H. Standinger and L. Ruzicka, Helv. Chim. Acta, 7, 177, 1924).

As can clearly be seen from the above examples, it has been believed almost impossible to obtain optically active allethrolone industrially.

The inventors, however, as a result of the long-term study, have succeeded in development of both the preparation of optically active allethronyl acid phthalate and the hydrolysis of the half-ester to allethrolone.

In other words, the inventors discovered that allethronyl acid phthalate could be resolved via diastereoisomeric salt with optically active amine.

The method of the present invention can be carried out as follows;

(A) diastereoisomeric salt formation by reacting 1 mole of (±)-allethronyl acid phthalate alone or with partially optically active allethronyl acid phthalate, with 0.5 to 1.5 mole of an optically active amine; (i) α-phenylethylamine, (ii) α-phenyl-β-p-tolylethylamine, (iii) threo-2-dimethylamino-1-(p-nitrophenyl)-1,3-propanediol, or (iv) naphthylethylamine, in an inert solvent; (B) crystallization and, if necessary, by further recrystallization to give the pure salt, corresponding to the resolving agents, (i) (−)-allethronyl acid phthalate-(+)-α-phenylethylamine salt or (+)-allethronyl acid phthalate-(−)-α-phenylethylamine salt, or (ii) (−)-allethronyl acid phthalate-(−)-α-phenyl-β-p-tolylethylamine salt or (+)-allethronyl acid phthalate-(+)-α-phenyl-β-p-tolylethylamine salt, or (iii) (−)-allethronyl acid phthalate-D(−)-threo-1-(p-nitrophenyl)-2-N,N-dimethylaminopropane-1,3-diol salt or (+)-allethronyl acid phthalate-L(+)-threo-1-(p-nitrophenyl)-2-N,N-dimethylaminopropane-1,3-diol salt, or (iv) (−)-allethronyl acid phthalate-(−)-naphthylethylamine salt or (+)-allethronyl acid phthalate-(+)-naphthylethylamine salt, and finally (C) decomposition of the resolved salt in the usual way with an acid or base to obtain (−)-allethronyl acid phthalate or its (+)-isomer, with simultaneous recovery of the optically active amine; α-phenylethylamine, α-phenyl-β-p-tolylethylamine, threo-1-(p-nitrophenyl)-2-N,N-dimethylaminopropane-1,3-diol or naphthylethylamine.

The inert solvent used in (A) includes hydrocarbon such as benzene, toluene or hexane, chlorinated hydrocarbon such chloroform, tetrachloromethane or chlorobenzene dichloroethane or tetrachloroethylene, ethers such as ethyl ether or isopropyl ether, ketones such as acetone, methyl ethyl ketone, methyl isobutyl ketone or diisobutyl ketone, esters such as ethyl acetate or lower alkyl alcohols such as methanol, ethanol, propanol or isopropyl alcohol, the mixture thereof or aqueous mixture thereof.

The (±)-allethronyl acid phthalate used as a starting material can be prepared according to known method (La Forge et al., J. Am. Chem. Soc., 74, 5392, 1952) or by the reaction between allethrolone and phthalic anhydride in the presence of a tertiary amine such as triethylamine.

The hydrolysis of allethronyl acid phthalate, unexpectedly proceeds very smoothly by heating in water or in an aqueous solvent, and allethrolone can be regenerated in a good yield. If necessary, the hydrolysis can be accelerated by the addition of a suitable amount of base.

In this process, if optically active allethronyl acid phthalate is used as the starting material optically active allethrolone can be obtained without racemization.

The present invention is further illustrated by the following non-limitative examples.

EXAMPLE 1

To the solution of 16.0 g of (±)-allethronyl acid phthalate and 6.4 g of (+)-α-phenylethylamine dissolved in 55 g of benzene, was added 18 g of n-hexane. After standing at room temperature, the precipitated crystallites were filtered to obtain 8.0 g of a crude salt (m.p. 111° ~ 113°C). The salt was recrystallized from the same mixture of benzene and n-hexane to give 6.0 g of white crystals; m.p. 115° ~ 116°C, $[\alpha]_D^{22}$ −17.8° (in ethanol). The purified salt was added into a cold 2% aqueous sodium bicarbonate solution to separate free (+)-α-phenylethylamine which was extracted with benzene. The aqueous layer was made acidic with conc. hydrochloric acid, and the separated oily matter was extracted with ether. The ether layer was washed with water, dried over anhydrous magnesium sulfate, and concentrated under a reduced pressure to give 4.1 g of (−)-allethronyl acid phthalate as a very viscous, oily material; $[\alpha]_D^{22}-45.9°$ (in ethanol).

EXAMPLE 2

18.0 g of (±)-allethronyl acid phthalate and 12.6 g of (−)-α-phenyl-β-p-tolylethylamine were dissolved in 60 ml of toluene, and the solution was allowed to stand overnight at a room temperature. The precipitated crystal was filtered and washed with toluene to give 8.0 g of white prisms (m.p. 126° ~ 128°C). The salt was cleaved with an 1% hydrochloric acid to separate free (−)-allethronyl acid phthalate which was then extracted with ether. The aqueous layer was basified with 5% aqueous caustic soda and oily (−)-α-phenyl-β-p-tolylethylamine was recovered. The ether layer was washed with water, dried and concentrated under a reduced pressure to give 4.60 g of (−)-allethronyl acid phthalate as a very viscous oil; $[\alpha]_D^{22}-49.6°$ (in ethanol).

EXAMPLE 3

18.0 g of (±)-allethronyl acid phthalate and 12.6 g of (−)-α-phenyl-β-p-tolylethylamine were dissolved in 80 ml of benzene, and the solution was allowed to stand overnight at a room temperature. The precipitates were filtered and washed with benzene to give 8.7 g of colorless crystal (m.p. 128° ~ 129°C). The salt was treated in the same manner as described in Example 1 to give 5.0 g of (−)-allethronyl acid phthalate as a very viscous oil; $[\alpha]_D^{22}-50.2°$ (in ethanol).

EXAMPLE 4

18.0 g of (±)-allethronyl acid phthalate and 12.6 g of (−)-α-phenyl-β-p-tolylethylamine were dissolved in 80 ml of a mixture of benzene and n-hexane (4 : 1), and the solution was allowed to stand overnight at a room temperature. The precipitated salt was filtered and washed (m.p. 123° ~ 126°C), and recrystallized from 80 ml of the above solvent to give 10.6 g of pure salt (m.p. 126.5° ~ 128°C). The salt was treated in the same manner as described in Example 1 to give 6.1 g of (−)-allethronyl acid phthalate as a very viscous oil; $[\alpha]_D^{22}-47.2°$ (in ethanol).

EXAMPLE 5

18.0 g of (±)-allethronyl acid phthalate and 14.4 g of D(−)-threo-1-(p-nitrophenyl)-2-N,N-dimethylamino-propane-1,3-diol were dissolved in hot mixture of 60.0 g of isopropylether and 80.0 g of methanol, and the solution was allowed to cool to a room temperature. The precipitates were filtered and recrystallized twice from the same solvent to give 10.10 g of pure salt; m.p. 98° ~ 101°C, $[\alpha]_D^{22}-33.51°$ (in methanol). The salt was cleaved with 1% hydrochloric acid to separate free (−)-allethronyl acid phthalate which was extracted with ether. The ether layer was washed with water, dried over anhydrous magnesium sulfate and concentrated 5.50 g of (−)-allethronyl acid phthalate was obtained as a very viscous oil; $[\alpha]_D^{22}-47.3°$ (in ethanol).

EXAMPLE 6

To a hot mixture of toluene (80 g) and n-hexane (30 g) was added 18.0 g of (±)-allethronyl acid phthalate and 10.3 g of (−)-α-(2-naphthyl)-ethylamine, and the mixture was allowed to cool to a room temperature. The precipitated salt was filtered, washed with the above mixed solvent, and dried in a desiccator to give 6.50 g of colorless crystal; m.p. 113° ~ 115°C, $[\alpha]_D^{22}+9.93°$ (in ethanol).

The salt was cleaved with 1% hydrochloric acid to separate free (+)-allethronyl acid phthalate which was then extracted with ether. The ether layer was washed with water, dried over anhydrous magnesium sulfate and concentrated under a reduced pressure to give 4.10 g of (+)-allethronyl acid phthalate as a very viscous oil; $[\alpha]_D^{22}+41.7°$ (in ethanol).

What is claimed is:

1. A method for preparing optically active allethronyl acid phthalate, which comprises reacting (±)-allethronyl acid phthalate of the formula

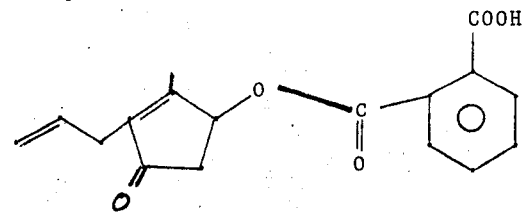

with an optically active amine selected from the group consisting of α-phenylethylamine of the formula

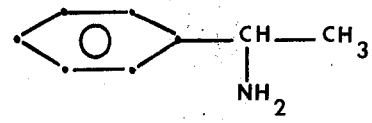

α-phenyl-β-p-tolylethylamine of the formula,

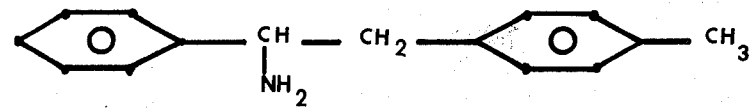

threo-2-dimethylamino-1-(p-nitrophenyl)-1,3-propanediol of the formula,

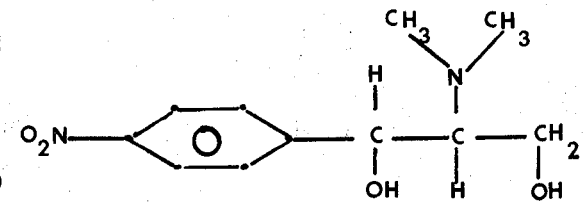

and naphthylethylamine of the formula

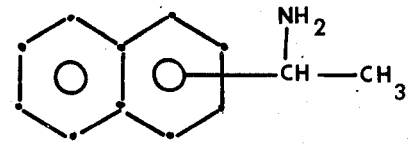

in the presence of a solvent selected from the group consisting of benzene, toluene, hexane, chloroform, tetrachloromethane, chlorobenzene, dichloroethane, tetrachloroethylene, ethylether, isopropylether, acetone, methylethyl ketone, methylisobutyl ketone, diisobutyl ketone, ethyl acetate, methanol, ethanol, propanol, isopropyl alcohol, a mixture thereof and an aqueous mixture thereof, the ratio of the optical active amine being 0.5 to 1.5 mole to 1 mole of the allethronyl acid phthalate, to form a diastereomeric salt thereof, and decomposing the resolved salt to obtain the optically active allethronyl acid phthalate.

2. A method according to claim 1, wherein the diastereomeric salt is decomposed with an acid or alkali.

* * * * *